(12) United States Patent
Kim et al.

(10) Patent No.: US 7,740,933 B2
(45) Date of Patent: Jun. 22, 2010

(54) PATTERNED, HIGH SURFACE AREA SUBSTRATE WITH HYDROPHILIC/HYDROPHOBIC CONTRAST, AND METHOD OF USE

(75) Inventors: Ho-Cheol Kim, San Jose, CA (US); Robert Dennis Miller, San Jose, CA (US)

(73) Assignee: International Business Machines Corporation, Armonk, NY (US)

(*) Notice: Subject to any disclaimer, the term of this patent is extended or adjusted under 35 U.S.C. 154(b) by 285 days.

(21) Appl. No.: 11/760,287

(22) Filed: Jun. 8, 2007

(65) Prior Publication Data
US 2007/0231559 A1    Oct. 4, 2007

Related U.S. Application Data

(62) Division of application No. 10/421,161, filed on Apr. 22, 2003, now Pat. No. 7,282,241.

(51) Int. Cl.
*B32B 3/26* (2006.01)
*H01L 21/00* (2006.01)
*C12Q 1/68* (2006.01)

(52) U.S. Cl. .................. 428/304.4; 438/1; 435/6

(58) Field of Classification Search ......... 428/304.4, 428/1; 435/6
See application file for complete search history.

(56) References Cited

U.S. PATENT DOCUMENTS 7,056,840 B2 * 6/2006 Miller et al. ............... 438/781
7,112,617 B2 * 9/2006 Kim et al. ................. 522/83

* cited by examiner

*Primary Examiner*—Victor S Chang
(74) *Attorney, Agent, or Firm*—Daniel E. Johnson

(57) ABSTRACT

Nanoporous structures are constructed that have hydrophilic regions separated by hydrophobic regions. The porous, hydrophilic regions have reaction sites suitable for use in a bioassay application and have a higher density of reaction sites than that of a non-porous (2-D) surface. The structure may be made by depositing a layer of a matrix material (e.g., an organosilicate) and a porogen, and then crosslinking the matrix material to form a nanohybrid composite structure. The porogen is decomposed to form pores within the matrix material, and a reactive gas phase species (e.g., ozone) is patternwise directed onto a surface of the matrix material. Ultraviolet light (directed through a mask) activates the gas phase species to form a reactive species that then reacts with the matrix material to make it hydrophilic. The porogen may be decomposed thermally or by exposing it to an oxidizing atmosphere in the presence of ultraviolet light.

24 Claims, 7 Drawing Sheets

PATTERNED, HIGH SURFACE AREA SUBSTRATE WITH HYDROPHILIC/HYDROPHOBIC CONTRAST, AND METHOD OF USE

This application is a divisional of, and claims priority to, Applicant's co-pending application Ser. No. 10/421,161 filed Apr. 22, 2003 and entitled "Patterned, high surface area substrate with hydrophilic/hydrophobic contrast, and method of use", which is hereby incorporated by reference.

TECHNICAL FIELD

The invention relates to a process of forming arrays patterned into regions of varying hydrophilicity, especially biomolecular arrays that have high areal density and offer high signal to noise ratios.

BACKGROUND

Biomolecular arrays have quickly developed into an important tool in life science research. Microarrays, or densely-packed, ordered arrangements of miniature reaction sites on a suitable substrate, enable the rapid evaluation of complex biomolecular interactions. Because of their high-throughput characteristics and low-volume reagent and sample requirements, microarrays are now commonly used in gene expression studies, and they are finding their way into significant emerging areas such as proteomics and diagnostics.

The reaction sites of the array can be produced by transferring to the substrate droplets containing biological or biochemical material. A variety of techniques can be used, including contact spotting, non-contact spotting, and dispensing. With contact spotting, a fluid bearing pin leaves a drop on the surface when the pin is forced to contact the substrate. With non-contact spotting, a drop is pulled from its source when the drop touches the substrate. With dispensing, a drop is delivered to the substrate from a distance, similar to an inkjet printer. Reaction sites on the array can also be produced by photolithographic techniques (such as those employed by Affymetrix or NimbleGen, for example).

The quality of the reaction sites directly affects the reliability of the resultant data. Ideally, each site would have a consistent and uniform morphology and would be non-interacting with adjacent sites, so that when a reaction occurred at a given site, a clear and detectable response would emanate from only that one site, and not from neighboring sites or from the substrate. To reduce the overall size of an array while maximizing the number of reaction sites and minimizing the required reagent and sample volumes, the sites on the array should have the highest possible areal density.

With current microarray technology, which is dominated by the use of flat substrates (often glass microscope slides), areal density is limited. To increase the signal from a given reaction site, the interaction area between the fluid (usually aqueous) and the substrate should be maximized. One way to do this is by using a surface that promotes wetting. A flat surface that promotes wetting, however, can lead to spots (and thus reaction sites) having irregular shapes and compositions. A flat wetting surface can also lead to the spreading of fluid from its intended site into neighboring sites. Thus, flat surfaces are intrinsically limited by fluid-surface interactions that force a tradeoff between the desired properties of the reaction sites.

To make the sites more uniform, the surface can be made non-wetting. Unfortunately, this reduces the interaction area between the fluid and the surface, thereby reducing the signal that would otherwise be obtainable. In addition, since droplets do not adhere well to a flat non-wetting surface, deposition volumes can vary from site to site, and droplets can slide away from their intended location, unless they are otherwise confined.

One way of avoiding the wetting vs. non-wetting dichotomy is to prepare surfaces that have regions of varying hydrophilic/hydrophobic contrast. Due to the aqueous environment of biomolecular arrays, patterned media having hydrophilic/hydrophobic contrast are ideal for confining bioactivity to within discrete regions defined by the pattern, with each discrete region in effect acting as an individual bioprobe. A hydrophobic surface is generally regarded as one having a static water contact angle of greater than 90 degrees, with decreasing contact angles resulting in progressively more hydrophilic surfaces. A surface having a water contact angle of less than 65 degrees is considered strongly hydrophilic. (For a discussion of contact angles, see A. W. Adamson et al., "Physical chemistry of surfaces", John and Wiley & Sons, New York, 1997.)

Several methods have been reported for preparing patterns of varying hydrophilicity, including traditional lithographic methods, imprinting, and contact printing. Lithographic techniques rely on the attachment of hydrophobic (or hydrophilic) molecules to preselected regions defined by photoresists in a hydrophilic (or hydrophobic) matrix. (See, for example, J. H. Butler et al., *J. Am. Chem. Soc.* 2001, 123, 8887.) With imprinting techniques, hydrophilic regions are created by pipetting droplets of a washable or hydrophilic lacquer, much like that in an ink-jet printer, and then converting the adjacent regions to hydrophobic regions. (See, for example, UK Patent Application GB 2340298AUK and Patent Application GB 2332273A.) Contact printing methods typically involve elastomeric stamps with hydrophilic (or hydrophobic) inks, with hydrophilic (or hydrophobic) patterns being generated as a result of transferring the ink onto a substrate. (See, for example, G. MacBeath et al, *Science* 2000, 289, 1760; and C. M. Niemeyer et al., *Angew. Chem. Int. Ed.* 1999, 38, 2865). U.S. Pat. No. 5,939,314 to Koontz discloses porous polymeric membranes having hydrophilic/hydrophobic contrast, in which the pore size is on the order of 0.1-2000 microns, but pores of this size are still relatively large. These methods generally involve, however, a series of several process steps.

A simple, more effective route to patterned substrate arrays having regions of varying hydrophilic/hydrophobic contrast would be highly desirable. Further, such arrays should have a high areal density of sites and high effective surface area to permit the collection of data with good signal/noise ratio. In addition, such an apparatus would ideally have sites of consistent and uniform spot morphology.

SUMMARY OF THE INVENTION

A simple and effective method is disclosed for generating films that include 3-D, nanoporous hydrophilic regions separated by hydrophobic regions. The porous, hydrophilic regions have reaction sites suitable for receiving reagents and/or reactants (biological, biochemical, or otherwise) that can be detected when tagged with a compound that fluoresces in response to irradiation with light (UV light, for example). The emitted fluorescence can then be detected by an optical detector. An advantage of porous material is that the density of potential reaction and/or absorption sites is significantly higher than that provided by a non-porous (2-D) surface. Patterning of the substrate may be accomplished by directing ultraviolet light onto a mask in the presence of a latent oxidizing species, such as ozone. Alternatively, an $O_2$-RIE process or oxygen plasma may be used in conjunction with a shadow mask to pattern the film.

An advantage of preferred methods disclosed herein is that the porosity of the films may be controlled by incorporating a pore-generating agent or compound (porogen) into a host material, followed by decomposition of the porogen. By utilizing porogen compounds in this manner, pore sizes and porosity can be tailored to the user's needs. One advantage of the UV/ozone treatments disclosed herein is that they are an economical way of producing reactive oxidizing species that can be utilized to produce regions of hydrophilic/hydrophobic contrast. Another advantage of the UV/ozone treatments is that the feature resolution (i.e., the spacing between adjacent hydrophobic and hydrophilic features) can be controlled optically.

One preferred implementation of the invention is a method of forming discrete hydrophilic regions on a substrate. The method includes depositing a layer onto a substrate, in which the layer includes a matrix material and a porogen, and then crosslinking the matrix material to form a nanohybrid composite structure out of the matrix material and the porogen. The method also includes decomposing the porogen to form pores within the matrix material, and patternwise directing a reactive gas phase species onto a surface of the matrix material. This forms discrete regions in the matrix material that are more hydrophilic than are other regions in the material that are adjacent to these discrete regions. The discrete (relatively more hydrophilic) regions and the other (preferably hydrophobic) regions extend from the surface of the material to beneath the surface of the material. The matrix material is preferably an organosilicate material, in which the nanohybrid structure is formed by crosslinking the organosilicate material. This crosslinking may induce phase separation between the organosilicate material and the porogen, or if a templating approach is used, the crosslinking of the organosilicate material is templated by the porogen. The crosslinking may be thermally induced, or it may be induced through a photochemical process, e-beam irradiation, or the addition of a basic or acidic catalyst to the organosilicate material. The gas phase species is advantageously directed onto the organosilicate material in a patternwise way, so that the discrete regions form a pattern within the organosilicate material. This pattern may be formed by a mask in proximity with the layer, with less hydrophilic regions in the organosilicate material corresponding to opaque portions of the mask. The gas phase species preferably includes an oxidizing species, such as ozone, with ultraviolet radiation activating the gas phase species to form a reactive species. The decomposition of the porogen may be thermally induced, or alternatively, this decomposition may be induced by exposing the porogen to an oxidizing atmosphere in the presence of electromagnetic radiation. The dimensions of the relatively more hydrophilic regions may be selected to be suitable for use in a biomolecular array. Because the pores are suitable for concentrating reagents and reactants (like those in a bioassay application), the dimensions of these hydrophilic regions may be chosen to be smaller than they otherwise would be in the absence of the pores.

One preferred implementation of the invention is a method of forming regions of varying hydrophilicity on a substrate. The method includes depositing a layer onto a substrate, in which the layer includes a matrix material and a porogen, and then crosslinking the matrix material to form a nanohybrid composite structure out of the matrix material and the porogen. The method further includes thermally decomposing the porogen to form pores in the layer, and patternwise oxidizing the matrix material to form regions of varying hydrophilicity within the layer, with these regions extending from a surface of the material into the material itself (e.g., 10 microns or less). This patternwise oxidizing may include directing, in the presence of a gas phase species such as ozone, ultraviolet radiation through a mask that is in proximity with the layer. The regions preferably include discrete hydrophilic regions separated by hydrophobic regions.

Another preferred implementation of the invention is a method of forming regions of varying hydrophilicity on a substrate. The method includes depositing a layer onto a substrate, in which the layer includes a matrix material and a porogen. The method further includes crosslinking the matrix material to form a nanohybrid composite structure out of the matrix material and the porogen, and patternwise directing (in the presence of an oxidizing species such as ozone) ultraviolet radiation onto selected regions of the matrix material to both decompose the porogen and induce hydrophilicity within the selected regions, with these selected regions extending from a surface of the matrix material into the material. The matrix material is preferably an organosilicate, with the crosslinking including thermally crosslinking the matrix material. The selected regions are preferably hydrophilic regions surrounded by hydrophobic regions.

One preferred embodiment is a nanoporous structure having regions of varying hydrophilicity, in which the regions correspond to a preselected pattern. The structure includes pores having a minimum characteristic dimension of between 2 nm and 75 nm, with these pores constituting at least 5% of the structure by volume. These regions of varying hydrophilicity preferably include discrete hydrophilic regions separated from each other by hydrophobic regions. The thickness of these regions may be less than 10 microns, e.g., between 0.5 and 10 microns, with the regions having a characteristic dimension between 2 microns and 1000 microns. In another preferred embodiment, the pores constitute at least 30% of the structure by volume.

BRIEF DESCRIPTION OF THE FIGURES

FIGS. 1A, 1B, 1C, 1D, 1E, 1F, and 1G, illustrates steps that may be used in forming a layer that includes porous, hydrophilic regions surrounded by hydrophobic regions, in which the sequence of steps represented by FIGS. 1A, 1B, 1C, 1D, and 1E represents one preferred method, and the sequence of steps represented by FIGS. 1A, 1B, 1F, and 1G represents another preferred method.

DETAILED DESCRIPTION OF THE INVENTION

Figure 1:
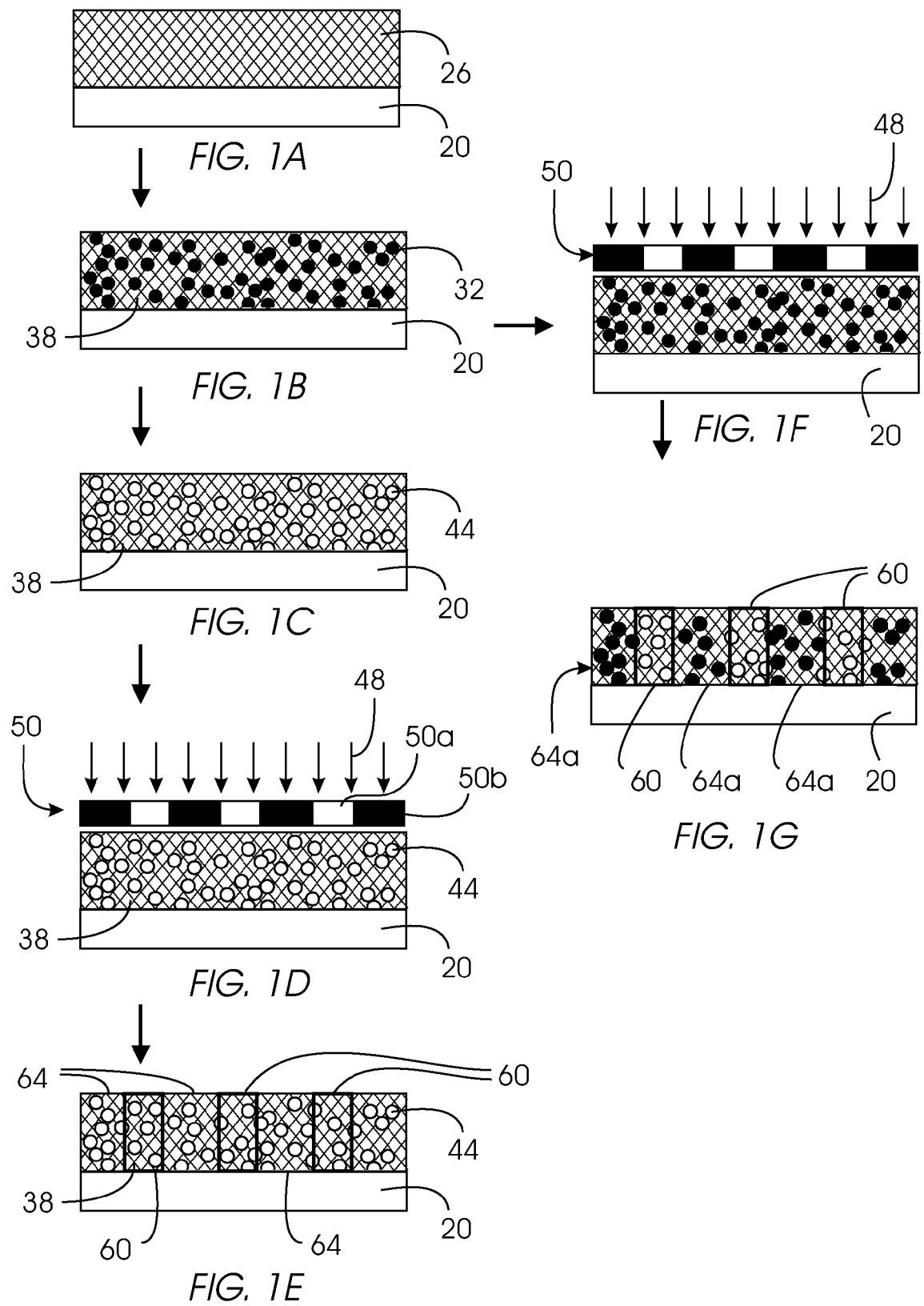
FIG. 1, which includes

Methods are disclosed herein for generating 3-D, nanoporous structures having regions of varying hydrophilic/hydrophobic contrast, e.g., alternating hydrophilic and hydrophobic regions. In one preferred method, a patterned nanoporous organosilicate is formed by first forming pores within a layer and then patterning the porous layer into regions of varying hydrophilicity. In another preferred method, a single process step is employed to make preselected regions of a substrate both porous and relatively hydrophilic with respect to adjacent regions in the substrate.

FIG. 1A shows a substrate 20 onto which a solution is applied. The substrate may be silicon, silicon dioxide, fused glass, ceramic, metal, or any other suitable material. The solution preferably includes a host matrix material (such as an organosilicate) and a decomposable porogen dissolved in a suitable solvent (e.g., 1-methoxy-2-propanol acetate). The porogen may be chemically bonded to the matrix material either directly or through a coupling agent, as discussed in U.S. Pat. No. 6,107,357 issued Aug. 22, 2000 to Hawker et al., which is hereby incorporated by reference. The solution may be applied to the substrate 20 by spraying, spin coating, dip coating, or doctor blading, so that a uniform thin film 26 of a porogen/matrix material mixture remains on the substrate 20 after the solvent has evaporated. Preferred matrix materials include organosilicates, such as those disclosed in U.S. Pat. No. 5,895,263 issued Apr. 20, 1999 to Carter et al. (which is hereby incorporated by reference), including the family of organosilicates known as silsesquioxanes, $(RSiO_{1.5})_n$. Suitable silsesquioxanes for the present invention include hydrido (R=H), alkyl (R=methyl), aryl (R=phenyl) or alkyl/aryl, as well as polymethylsilsesquioxane (PMSSQ), which are commercially available from Dow Corning, Techneglas, LG Chemicals, and Shin-Etsu, for example. Other suitable matrix materials include polysilanes, polygermanes, carbosilanes, borozoles, carboranes, the refractory oxides, amorphous silicon carbide, and carbon doped oxides. Suitable decomposable porogens include linear polymers, crosslinked polymeric nanoparticles, block copolymers, random copolymers, dendritic polymers, star polymers, hyperbranched polymers, grafts, combs, unimolecular polymeric amphiphiles, and porogens such as those discussed in U.S. Pat. No. 5,895,263 to Carter et al.

As illustrated in FIG. 1B, a nanohybrid composite structure between the porogen 32 and the matrix 38 is then formed, so that the porogen is entrapped in the crosslinked matrix. Different processes may be employed to arrive at this stage, such as i) a nucleation and growth process and ii) a particle templating process. In a nucleation and growth process, the sacrificial porogen is miscible in the matrix material before curing and phase separates upon the crosslinking of the matrix material to form polymer-rich domains. (Crosslinking is preferably accomplished by heating the matrix material, although other ways of initiating crosslinking are possible, such as photochemical means, e-beam irradiation, and the addition of a basic or acidic catalyst to the organosilicate material.) Ideally, the domains remain nanoscopic due to low mobility in the viscous, crosslinking matrix, and these domains ultimately become the pores. The morphology and size of the pores depends on the loading level of the porogen (i.e., how much porogen is present in the matrix prior to decomposition of the porogen), the porogen molecular weight and structure, resin structure, processing conditions, and so on. Although small pores can be generated, the process has many variables.

In a porogen templating process, on the other hand, the porogen is never really miscible in the matrix, but is instead dispersed. The matrix crosslinks around the porogen, so that the porogen templates the crosslinked matrix. (Below the percolation threshold, the porous morphology is composition independent, one porogen molecule generates one hole, and pore size depends on the porogen size. Therefore, it is advantageous to work above the percolation threshold, so that interconnected pores are formed.) Templating behavior is observed in the acid-catalyzed hydrolytic polymerization of tetraethoxysilane (TEOS) in the presence of surfactant molecules (see R. D. Miller, Science, 1999, 286, 421 and references cited therein). The surfactant molecules form dynamic supermolecular structures which upon processing template the crosslinked matrix material. Templating behavior is often observed for highly crosslinked nanoparticles generated by suspension (see M. Munzer, E. Trommsdorff, Polymerization in Suspension, Chapter 5 in Polymerization Processes, C. F. Schieldknecht, editor, Wiley Interscience, New York, 1974) or emulsion polymerization (see D. H. Blakely, Emulsion Polymerization: Theory and Practice, Applied Science, London, 1965); these are classified as top down approaches to porogen synthesis. Bottom up approaches to crosslinked nanoparticles are also possible, and may involve the intramolecular crosslinking collapse of a single polymer molecule to produce a crosslinked nanoparticle (see D. Mercerreyes et al., Adv. Mater. 2001, 13(3), 204; and E. Harth et al., J. Am. Chem. Soc., 2002, 124, 8653). A bottom up templating approach may also be observed for un- or lightly-crosslinked materials which exhibit particle-like behavior in the matrix, e.g., with multiarm star-shaped polymeric amphiphiles where the core and shell portions have widely different polarity. In this case, the inner core collapses in the matrix material while the polymer corona stabilizes the dispersion to prevent aggregation (see U.S. Pat. No. 6,399,666 issued Jun. 4, 2002 to Hawker et al., which is hereby incorporated by reference). Each of these porogen classes (surfactant, top down, and bottom up) may be used to template the crosslinking of, for example, PMSSQ.

Thus, more than one approach may be used to generate the porogen phase 32 within the matrix 38 shown in FIG. 1B. For systems displaying nucleation and growth characteristics, the matrix 38 (e.g., the organosilicate) and the porogen 32 are subjected to a phase separation process. A preferred way of inducing this phase separation is by heating the (preferably thin, <5 microns) film 26 to the crosslinking reaction temperature of the organosilicate, thereby forming a nanohybrid composite of the porogen and organosilicate in the film, so that an organic, porogen phase 32 is entrapped in an inorganic, crosslinked matrix 38. Alternatively, a templating approach may be used, as discussed above, in which a suitable porogen 32 is dispersed but is not miscible in an appropriate matrix 38, which is then thermoset (upon application of heat, for example) to form a nanohybrid structure. Regardless of which approach is used (nucleation/growth or templating), the loading level of the porogen is preferably high enough that the percolation threshold is reached in the nanohybrid composite and porous film so derived, so that the pores 44 are highly interconnected (not shown in the cross sectional views of FIG. 1). When the pores 44 are interconnected in this manner, the effective surface area of the end product (corresponding to FIG. 1E or 1G) is high, and the interconnectivity of the pores facilitates accessibility to reactants and reagents. This permits good signal/noise ratio data in a biodetection application. To this end, a porogen loading of 30 wt. % or more is preferred, resulting in an end product whose volumetric porosity is approximately 30%.

At this point, more than one approach may be employed to produce a nanoporous structure having regions of varying hydrophilic/hydrophobic contrast, as indicated by the two pathways corresponding to FIGS. 1C and 1F, respectively. Either of these pathways, however, may be used to generate interconnected pores that preferably have an average characteristic minimum dimension (e.g., a diameter) of between 2 nm and 75 nm, and still more preferably between 2 nm and 50 nm. Pores of this size are advantageous in that they offer the user high effective surface area and access to reagents and reactants. In FIG. 1C, additional heat is applied to the film to bring it to a temperature above the decomposition temperature of the porogen, e.g., the film may be heated to 350° C. or above in an inert atmosphere. This results in the thermal decomposition of the phase-separated porogen 32, so that the space occupied by the porogen becomes voids 44 or pores. This approach to the generation of a nanoporous film, known as the sacrificial porogen (pore generator) approach, relies on the selective removal of the organic macromolecular (porogen) phase from phase-separated mixtures of organic (or inorganic) polymers. (Further details on porogens may be found in U.S. Pat. No. 5,895,263 to Carter et al., for example.) The morphology and dimensions of the pores 44 are determined mainly by the interaction between the porogen (the dispersed phase 32), the organosilicate matrix 38, and the composition of these mixtures. In general, with increasing porogen loading level (i.e., increasing weight percentage of the porogen in the organosilicate prior to decomposition of the porogen), the pores formed in the organosilicate become increasingly interconnected: For low porogen loading (<20%), a closed cell structure is observed, whereas for higher porogen loading, interconnected or bicontinuous phase structures are observed. Using the methods described herein, end products may be obtained whose volumetric fraction of pores is between 5% and 80%, and more preferably between 30% and 70%.

The film may then be exposed to ultraviolet (UV) light in the presence of ozone ($O_3$), as indicated by the arrows 48 of FIG. 1D, to generate regions of varying hydrophilicity. By patternwise exposing the film through use of a mask 50, regions of the film that are so exposed become relatively more hydrophilic regions 60, as shown in FIG. 1E. As an alternative to the UV/ozone process (in which $O_3$ is photodissociated by UV light to generate atomic oxygen, which is a reactive species), a UV/$N_2O$ process (in which $N_2O$ is photodissociated by UV light to generate atomic oxygen) or a UV/$H_2O_2$ process (in which $H_2O_2$ is photodissociated by UV light to generate the hydroxyl radical, which is also a reactive species) may be used in conjunction with a mask 50. Other sources of hydroxy, alkoxy, and aryloxy radicals may be used instead of $H_2O_2$, such as $RO_2H$, $RO_2R'$, and $RCO_3R'$, in which R and R' are alkyl or aryl substituents.

The portions of the mask 50 shown as darkened regions represent opaque portions 50b of the mask, and the lighter regions represent portions 50a of the mask that are open spaces or at least transparent to UV light. (For example, if the portions 50a are quartz, the mask 50 may be located slightly above the film, with ozone being passed between the mask and the film. Alternatively, the mask 50 may be placed in direct contact with the film, with ozone being diffused directly through the porous film.) On the other hand, those regions 64 of the film that remain unexposed to UV, and therefore unexposed to reactive oxygen (i.e., those regions shielded by the opaque portions 50b), remain hydrophobic. The mask 50 can be metallic (e.g., chromium, copper, brass, or beryllium-copper) and is positioned above the film, preferably in direct contact with the film, to facilitate good spatial contrast between the relatively hydrophilic regions 60 and the surrounding hydrophobic regions. Masks similar to those used in the photolithography industry may be employed, with a spatial resolution (the distance between the opaque portions 50b and the open portions 50a) being less than 1 micron, for example. As an alternative to the UV/ozone treatment, an oxidizing plasma (e.g., $O_2$) may be directed onto a shadow mask. In another implementation, an $O_2$—RIE process in combination with a shadow mask may be used to form the hydrophilic regions 60, or any direct-write oxidizing source (e.g., an ion beam) may be used for this purpose.

Figure 2:
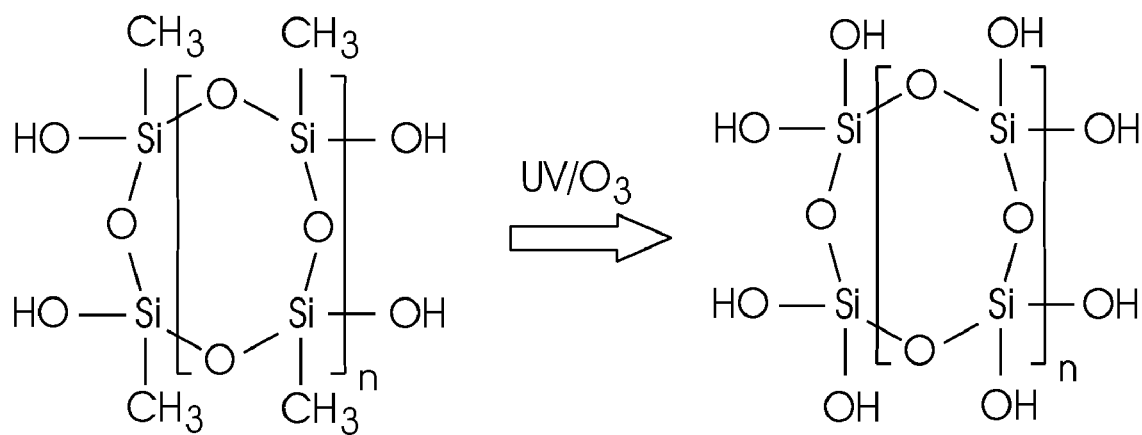
FIG. 2 is a schematic illustration of how functional groups in polymethylsilsesquioxane (PMSSQ) are modified as a result of exposure to ultraviolet light and ozone.

The chemical mechanism leading to the desired hydrophilicity can be at least partially explained as follows. Generally, it is known that ozone is "activated" to produce a reactive species (atomic oxygen) upon absorption of UV light (e.g., the 253.7 nm Hg line may be used to photodissociate ozone). Atomic oxygen is postulated to be an etching species, which, over a wide range of temperatures (e.g., from room temperature to ~300° C. and higher), is capable of breaking organic materials into simple, volatile oxidation products such as carbon dioxide, water, and so on. It is believed that the UV/ozone treatment (or alternatively, the UV/$N_2O$ treatment or the UV/$H_2O_2$ treatment discussed above) eliminates matrix methyl groups (—$CH_3$) from the PMSSQ and introduces a polar oxidation product, namely hydroxyl groups (—OH), as shown in FIG. 2. FTIR spectroscopy measurements reveal that a prominent absorption band at 3400 $cm^{-1}$ arises as a result of the UV/ozone treatment, suggesting that hydroxyl groups are present in the UV/ozone treated sample. Thus, the silicon species left behind after oxidation of PMSSQ contains a significant amount of polar SiOH functionality, which is known to be hydrophilic. Directing an oxidizing species onto other matrix materials, such as polysilanes, polygermanes, carbosilanes, borozoles, carboranes, the refractory oxides, amorphous silicon carbide, and carbon doped oxides, also leads to the formation of —OH.

As an alternative to the series of steps illustrated by FIGS. 1C, 1D, and 1E, the steps illustrated by FIGS. 1F and 1G may be used after the phase separation of FIG. 1B. In FIG. 1F, a UV/ozone treatment in combination with a mask 50 is used. This technique generates porous, hydrophilic regions 60 separated from non-porous, hydrophobic regions 64a, as shown in FIG. 1G. In this case, the UV/ozone treatment decomposes the organic, porogen phase 32 (into $CO_2$, $H_2O$, and lower molecular weight oxidized fragments) while simultaneously changing the chemical property of the organosilicate to produce hydrophilic regions 60. (For this reason, the regions 50a in the mask of this implementation are preferably open spaces that allow the decomposing porogen to diffuse out of and away from the film.) This approach is advantageous in that fewer process steps are involved than the approach that includes the steps illustrated by FIGS. 1C, 1D, and 1E. Furthermore, the step illustrated by FIG. 1F allows the user to control how far into the film pores 44 are formed by controlling the ozone concentration, ultraviolet light intensity, temperature, and/or exposure time. Increasing any one of these three variables tends to form pores deeper into the film, and thereby tailor the volume available to the user, e.g., in a biodetection experiment.

The methods disclosed herein may be used to form porous films having a thickness of up to at least 1 micron. Film thicknesses in the ranges of 0.5-1 micron, 0.5-2 microns, 0.5-3 microns, 0.5-4 microns, 0.5-5 microns, 0.5-10 microns or more may also be realized. In addition, well-defined feature sizes as small as about 4 microns may be obtained, as discussed in Example 4 below. Feature sizes in the ranges of 2-4 microns, 2-10 microns, 2-50 microns, 2-1000 microns, 4-50 microns, 4-75 microns, 4-500 microns, and 4-1000 microns may also be realized.

The hydrophilic/hydrophobic patterning techniques described herein may be used to form 3-D porous structures or be applied to non-porous structures yielding surfaces of hydrophilic/hydrophobic contrast. For example, the UV/ozone technique (and the UV/$H_2O_2$ and UV/$N_2O$ techniques) may be applied to form (non-porous or nominally porous) surfaces that are patterned into hydrophilic and hydrophobic regions. Such surfaces can be used in a biodetection application. Materials that may be used in such a 2-D patterning technique (in addition to the matrix materials already described) include the family of silicon containing polymers that are not silicates or silicones, as well as carbon-containing polymers that do not contain silicon.

EXAMPLES

The porous PMSSQ of Examples 1-5 was formed by beginning with a mixture of 80 wt. % porogen (namely, the triblock copolymer of ethylene oxide and propylene oxide sold under the name "Pluronics" by the BASF company) and 20 wt. % organosilicate (namely, the polymethylsilsesquioxane GR650F from Techneglas, shown in FIG. 2) dissolved in the solvent 1-methoxy-2-propanol acetate. This solution was applied uniformly to a silica wafer by spin coating, so that a uniform thin film of the porogen/organosilicate mixture remained on the substrate 20 after the solvent had evaporated. A nanohybrid composite film was produced by heating the porogen/organosilicate mixture (at a temperature of between 150° C. and 250° C.) in an inert atmosphere.

For Examples 1-4, porosity in the nanohybrid composite film was then generated by heating it to 350° C. or higher. The porous film was then subjected to a UV/ozone treatment to generate regions of varying hydrophilicity. For Example 5, a UV/ozone treatment was applied to the nanohybrid composite film at a temperature of 30° C., which generated porosity in the film as well as regions of varying hydrophilicity.

The UV/ozone treatment for these examples was performed as follows. The oxygen flow rate into the ozone generator was 3.0 standard liters per min, thereby producing an ozone concentration of 38000 ppm by volume. For this purpose, a SAMCO International, Inc. UV/ozone stripper (model UV-300H) was used. The UV light source included two 235 watt hot cathodes, low-pressure, high-output mercury vapor lamps, having primary process wavelengths at 254 nm and 185 nm.

Example 1

Figure 3:
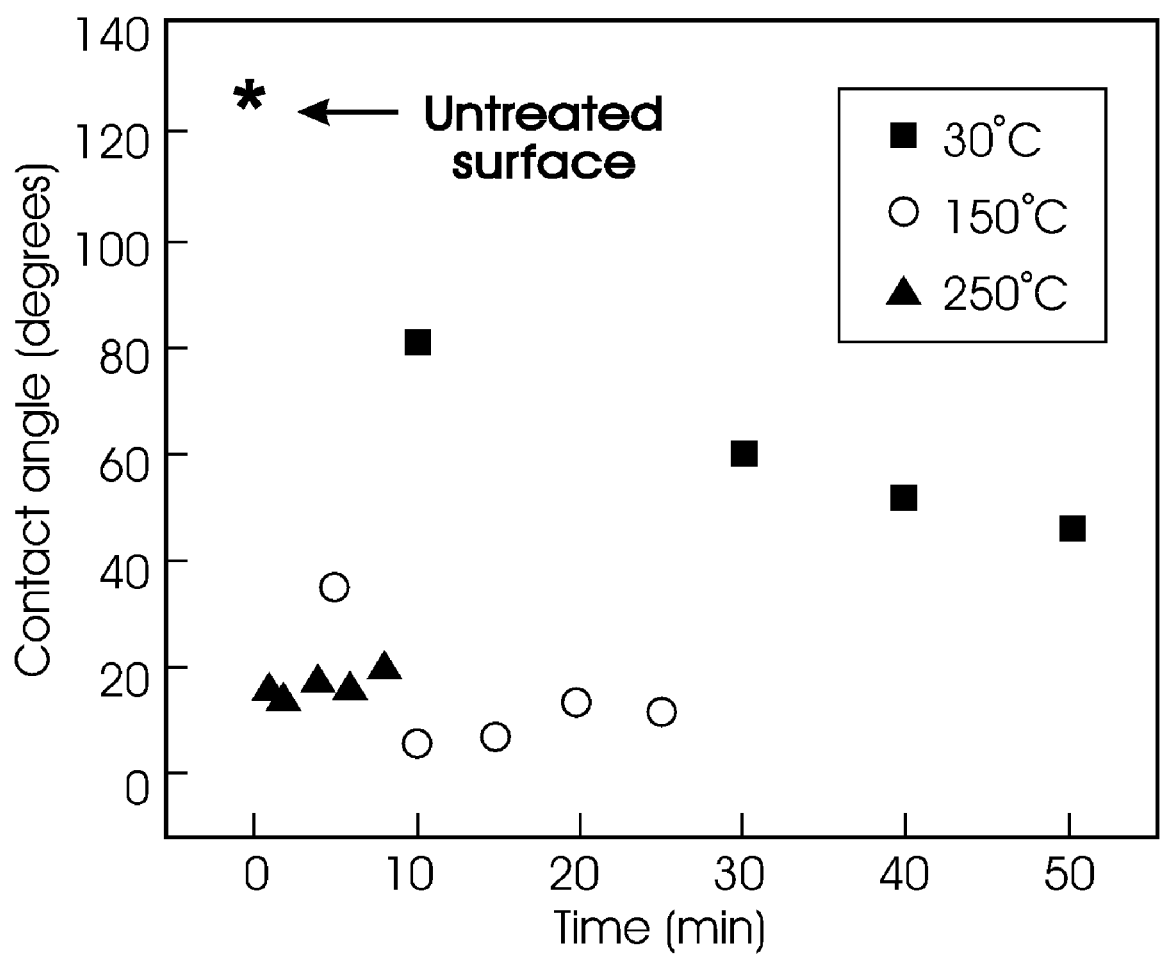
FIG. 3 illustrates the effect of temperature and exposure time on the static water contact angle of a layer of porous PMSSQ when the layer is exposed to ultraviolet light and ozone.

Static water contact angle measurements were made with an AST Video Contact Angle System 2500 XE to quantify the effect of UV/Ozone treatment (like that shown in FIG. 1D) on the surface properties of porous PMSSQ films (like that shown in FIG. 1C). FIG. 3 shows the contact angle as a function of treatment time for porous film produced from starting material of 80 wt. % porogen/20 wt. % organosilicate. (Films of 10, 30, and 50 wt. % porogen were examined as well, and gave substantially similar results; films with a higher initial wt. % of porogen have greater porosity following decomposition of the porogen.) There is a rapid decrease in the contact angle over time, indicating that the surface is becoming more hydrophilic. This phenomenon is accelerated at higher temperatures, as a comparison between the data at 30° C. and 150° C. shows. A still more rapid decrease in the contact angle was observed at 250° C. The water contact angle decreases from more than 100 degrees initially to 10 degrees or less (see the 150° C. data, for example). The contact angle data of FIG. 3 are clear evidence that the surface of the PMSSQ film becomes hydrophilic as a result of the UV/ozone treatment, and that the degree of this hydrophilicity can be controlled (e.g., by controlling treatment time and temperature) over the range from between 90 degrees down to about 10 degrees or less.

Example 2

Figure 4:
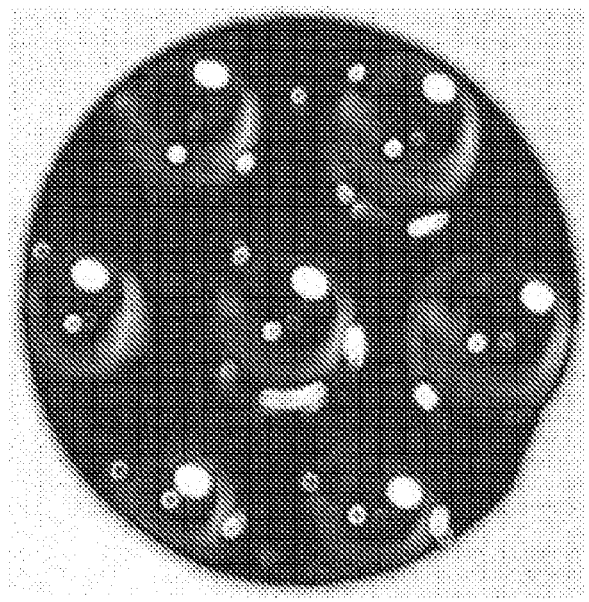
FIG. 4 is an image of drops of water on a 1" diameter layer of porous PMSSQ that has been patterned into hydrophobic and hydrophilic regions.

By limiting UV exposure to those areas on a film corresponding to open areas within a metal mask (as shown by the mask of FIG. 1D, for example), hydrophilic patterns in a hydrophobic matrix can be obtained. In this case, only those areas on the film exposed to both UV and ozone become hydrophilic, while unexposed areas remain hydrophobic. Masks or schemes which create patterns of UV light are useful for this patterning. The result of such a patterning process is demonstrated in FIG. 4, which shows porous PMSSQ (on a 1" silica wafer) on which water droplets are confined to ¼ inch diameter hydrophilic areas.

Example 3

When hydrophilic areas are reduced in size to the point that they have a characteristic dimension (i.e., an approximate width or length) of 250 microns or less, the surface tension of water prevents the formation of well-defined drops (like those shown in FIG. 4), so that only wavy shapes at the water/surface/air contact line are evident, indicating that probe molecules in aqueous solution can be confined to the hydrophilic patterned areas. Indeed, the surface hydroxyl groups generated by UV/Ozone treatment are themselves useful for chemical reactions for bonding probe molecules covalently.

Figure 5:
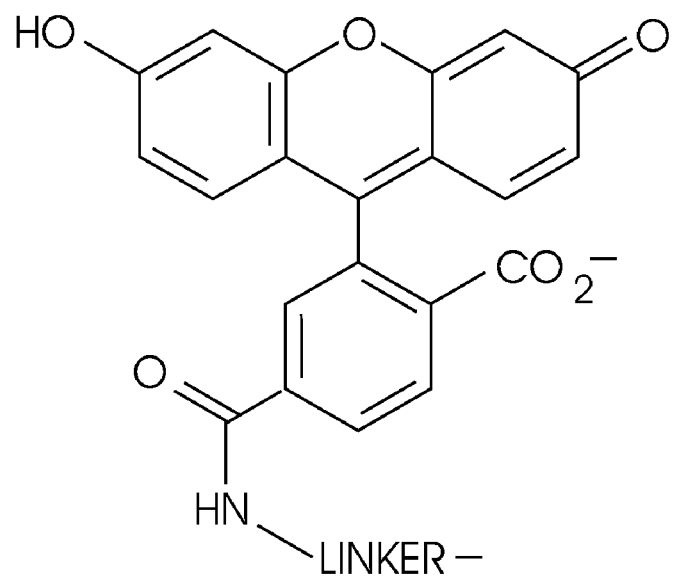
FIG. 5 illustrates a fluorescent dye structure attached to a linker that in turn was attached to a layer of porous PMSSQ that had been subjected to an ultraviolet light/ozone treatment.

To demonstrate that a higher number density of —OH groups is available within a i) UV/ozone treated porous organosilicate medium than either ii) a flat silica substrate that was not treated with UV/ozone or iii) non-porous MSSQ treated with UV/ozone, a fluorescent dye was used. Specifically, the linker 3-bis(2-hydroxyethyl) amino propyl triethoxysilane was attached to —OH groups on representative samples of i), ii), and iii). The fluorescent dye 6-carboxyfluorescein (commercially available from Applied Biosystems as 6-FAM™ amidite, for example) was then selectively attached to each of these samples, as indicated in FIG. 5. This dye fluoresces green in response to optical excitation.

Figure 6:
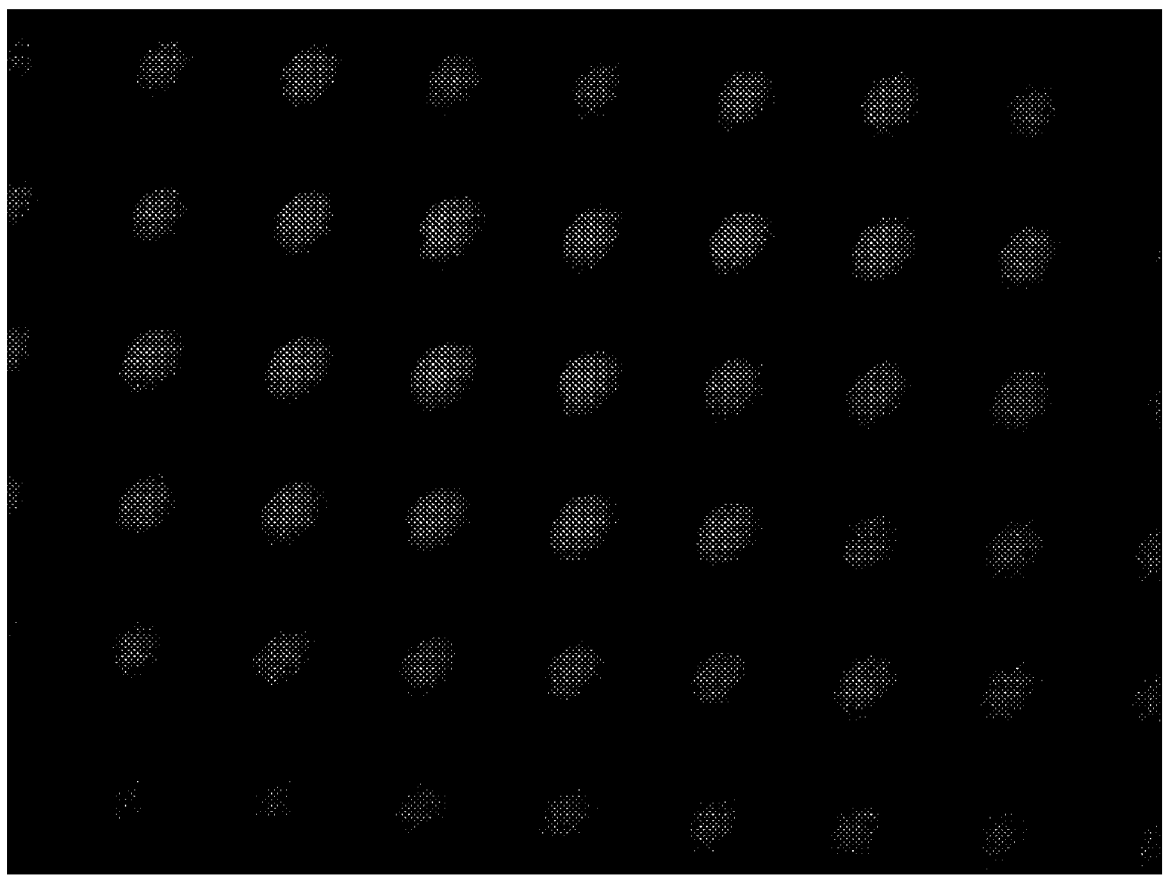
FIG. 6 is a fluorescence microscope image of a porous organosilicate surface that has been patterned into hydrophobic and hydrophilic regions, in which the hydrophilic regions have been tagged with the fluorescent dye of FIG. 5.

FIG. 6 shows a fluorescence microscope image of a porous, patterned surface (case i) to which the linker and fluorescent dye have been attached. Images were obtained using a fluorescence microscope, and the intensity of the fluorescent image was quantified using image analysis software. The image of FIG. 6 shows discrete regions where the dye has been selectively attached, with these regions corresponding to the patterned areas where surface SiOH functional groups have been generated. These discrete regions, which are clearly contrasted from the underlying matrix, are roughly circular and have a diameter of approximately 250 μm.

Continuing with this example, the fluorescence intensity (of green light) from these discrete, circularly shaped regions was compared with that from samples ii) and iii). The use of image analysis software suggests that the signal intensity was approximately 10 times higher signal intensity from porous PMSSQ surface (case i) than from a native oxide layer of a flat silicon wafer that was not treated by UV/ozone (case ii), and about 7 times higher than the signal from a non-porous PMSSQ surface exposed to the same UV/ozone treatment (case iii). The enhanced patterned fluorescence of the treated PMSSQ surface relative to native oxide shows that 2-D images can be produced in dense organosilicate films using the technique. The quantitative data are clear evidence of a volumetric effect, namely, that porous PMSSQ surfaces allow for a greater number density of attached molecules than do their non-porous counterparts, indicating that —OH groups are formed throughout the porous sample.

Example 4

Figure 7A:
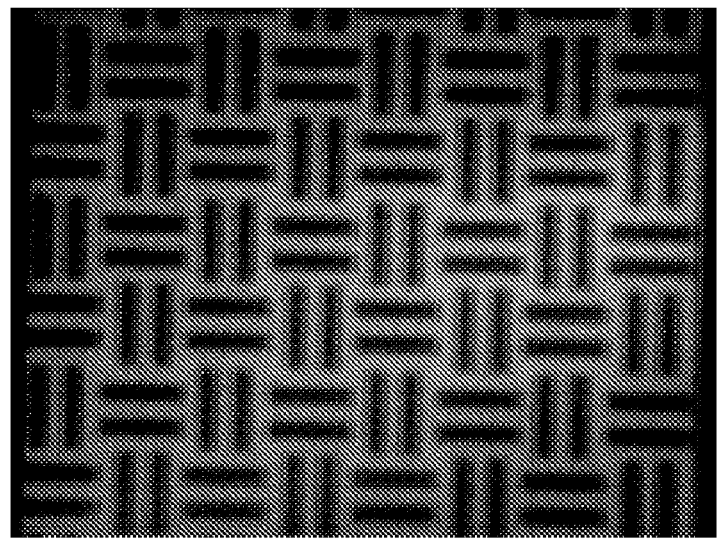
FIGS. 7A, 7B, and 7C are fluorescence microscope images of porous PMSSQ patterned into hydrophobic and hydrophilic regions, in which the smallest characteristic feature sizes (the line widths of the segments in the images) are 32, 16, and 8 micrometers, respectively.
Figure 7B:
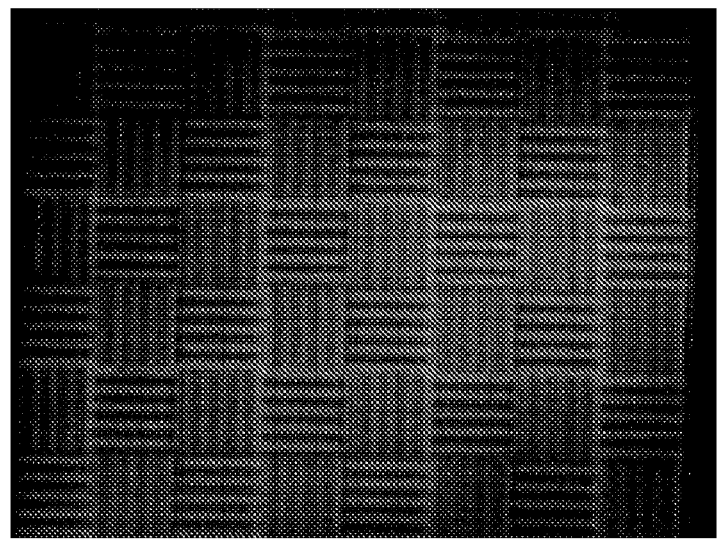
Figure 7C:
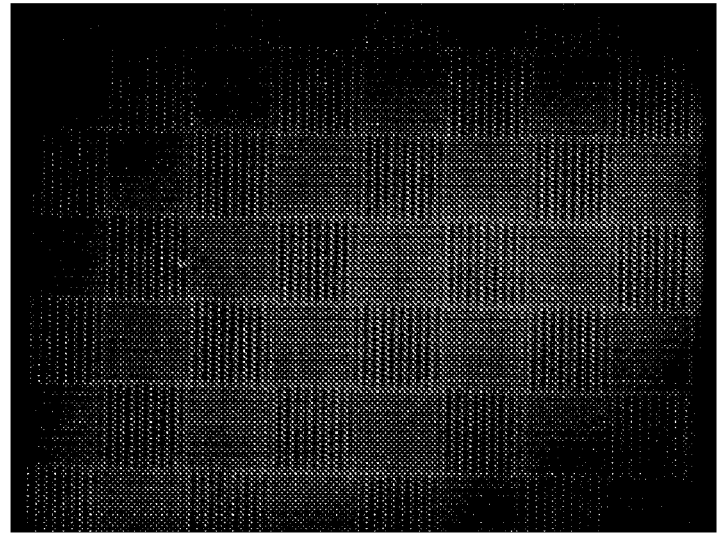

Photolithographic masks (of quartz and a chromium coating) having different features sizes were placed in direct contact with 750 nm thick porous PMSSQ film to make hydrophilic/hydrophobic patterns corresponding to the features of the masks. Fluorescent dye was attached to hydrophilic regions of the porous PMSSQ film, in a manner like that described above in connection with Example 3. FIGS. 7A, 7B, and 7C show darker (hydrophobic) regions and lighter, fluorescing (hydrophilic) regions, in which fluorescent dye has been attached to the hydrophilic regions. FIGS. 7A, B, and C show well defined patterns of 32, 16, and 8 µm feature sizes, respectively (corresponding to the width of the dark segments in these figures). For features sizes smaller than 4 µm, there was some evidence of smeared boundaries between the hydrophilic and hydrophobic regions, presumably due to diffusion of the active oxidizer before reaction with the matrix.

Example 5

Figure 8:
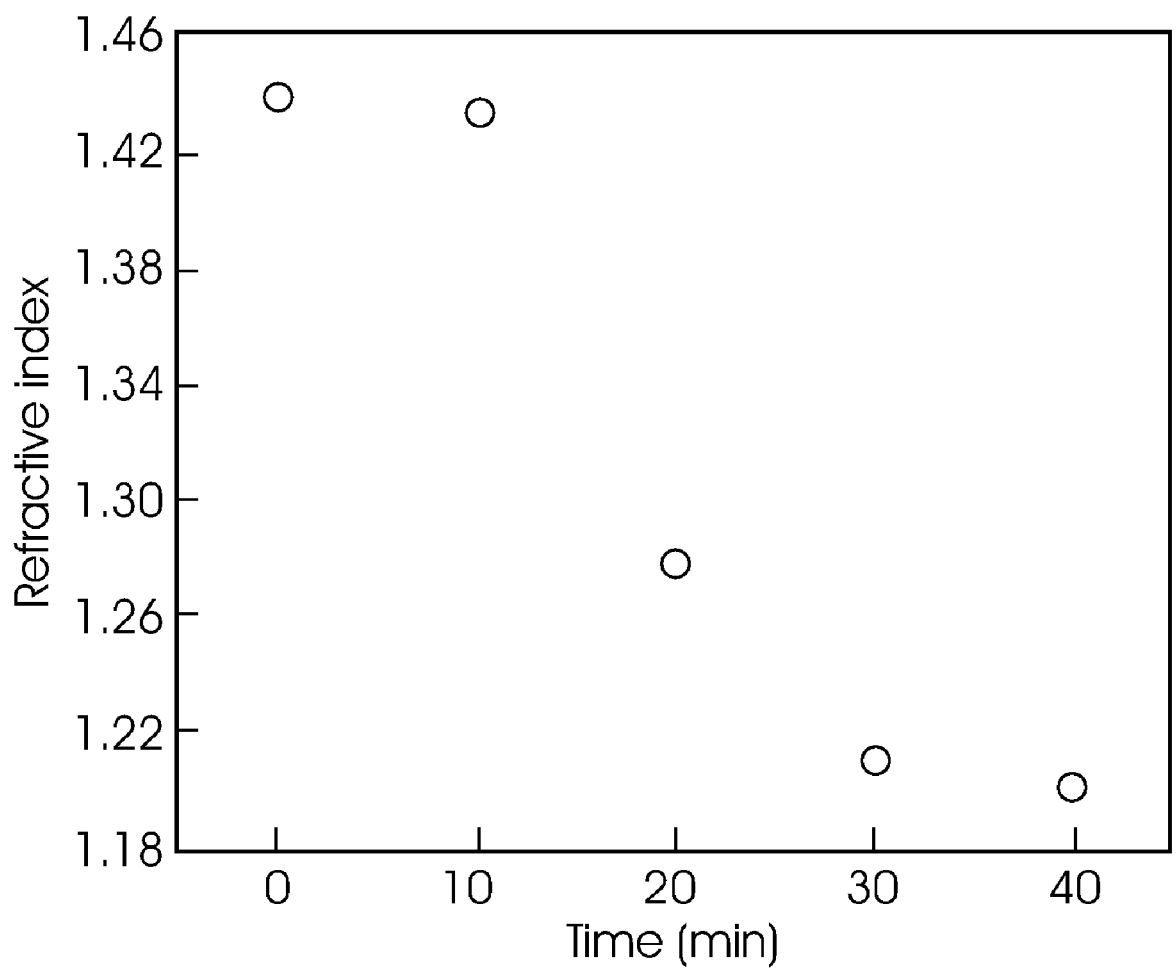
FIG. 8 shows how the refractive index of a nanohybrid composite film changes as a function of UV/ozone treatment time at temperature of 30° C.

The refractive index of a nanohybrid composite film was measured to quantify porogen decomposition as a function of UV/ozone treatment time. The temperature was held constant at 30° C. A white light interferometer (Filmetrics F20 Thin Film Measurement System) was used to measure the refractive index. FIG. 8 shows how the refractive index changes as a function of UV/ozone treatment time. Prior to any UV/ozone treatment (time=0 minutes), the nanohybrid composite film has a refractive index of 1.44. The refractive index decreases as the UV/ozone treatment is applied. This is attributed to decomposition of the porogen, leading to an increased volumetric fraction of air within the film. The refractive index reaches about 1.20 after 40 minutes of this treatment, which is very nearly equal to the index of refraction of a porous film whose porosity has been generated by thermal decomposition of the porogen.

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes within the meaning and range of equivalency of the claims are to be embraced within that scope.

What is claimed is:

1. A structure formed from material that has been patterned into regions of varying hydrophilicity, the regions corresponding to a preselected pattern and having a characteristic dimension of between 2 microns and 1000 microns, the regions including discrete hydrophilic regions of organosilicate material separated from each other by hydrophobic regions of organosilicate material, wherein the structure includes pores having a diameter of between 2 nm and 50 nm, and wherein the structure has a volumetric porosity of at least 30%.

2. A structure formed from material that has been patterned into regions of varying hydrophilicity, wherein the regions correspond to a preselected pattern, the structure includes pores having a diameter of between 2 nm and 75 nm, and the structure has a volumetric porosity of at least 5%.

3. The structure of claim 2, wherein the regions of varying hydrophilicity include discrete hydrophilic regions separated from each other by hydrophobic regions.

4. The structure of claim 3, wherein the thickness of the structure is less than 10 microns.

5. The structure of claim 3, wherein the thickness of the structure is between 0.5 and 10 microns.

6. The structure of claim 3, wherein the regions have a characteristic dimension between 2 microns and 1000 microns.

7. The structure of claim 3, wherein the structure has a volumetric porosity of at least 30%.

8. The structure of claim 3, wherein the regions have a characteristic dimension between 4 microns and 500 microns.

9. The structure of claim 3, wherein the regions have a characteristic dimension between 4 microns and 75 microns.

10. The structure of claim 3, wherein the regions have a characteristic dimension between 2 microns and 50 microns.

11. The structure of claim 3, wherein the thickness of the structure is at least one micron.

12. The structure of claim 3, further comprising a substrate on which the structure is formed.

13. The structure of claim 2, comprising porous, hydrophilic regions of organosilicate material separated from non-porous, hydrophobic regions of organosilicate material.

14. The structure of claim 2, comprising porous, hydrophilic regions of organosilicate material separated from porous, hydrophobic regions of organosilicate material.

15. A structure formed from material that has been patterned into regions of varying hydrophilicity, wherein the regions correspond to a preselected pattern, the structure includes pores having a diameter of between 2 nm and 50 nm, and the structure has a volumetric porosity of at least 5%.

16. The structure of claim 15, wherein the regions of varying hydrophilicity include discrete hydrophilic regions of organosilicate material separated from each other by hydrophobic regions of organosilicate material.

17. The structure of claim 16, wherein the thickness of the structure is between 0.5 and 10 microns.

18. The structure of claim 16, wherein the regions have a characteristic dimension between 2 microns and 1000 microns.

19. The structure of claim 16, wherein the structure has a volumetric porosity of at least 30%.

20. The structure of claim 16, wherein the regions have a characteristic dimension between 2 microns and 50 microns.

21. The structure of claim 16, wherein the thickness of the structure is at least one micron.

22. The structure of claim 16, further comprising a substrate on which the structure is formed.

23. The structure of claim 15, comprising porous, hydrophilic regions separated from non-porous, hydrophobic regions.

24. The structure of claim 15, comprising porous, hydrophilic regions separated from porous, hydrophobic regions.

* * * * *